United States Patent
Lee et al.

(10) Patent No.: US 11,305,116 B2
(45) Date of Patent: Apr. 19, 2022

(54) CURRENT MONITORING APPARATUS AND ELECTRICAL STIMULATION APPARATUS COMPRISING SAME

(71) Applicant: Y-BRAIN INC., Daejeon (KR)

(72) Inventors: Ki Won Lee, Seongnam-si (KR); Jong Min Jang, Suwon-si (KR); Byung Gik Kim, Daegu (KR)

(73) Assignee: Y-BRAIN INC., Daejeon (KR)

(*) Notice: Subject to any disclaimer, the term of this patent is extended or adjusted under 35 U.S.C. 154(b) by 241 days.

(21) Appl. No.: 16/399,003

(22) Filed: Apr. 30, 2019

(65) Prior Publication Data
US 2019/0255328 A1   Aug. 22, 2019

Related U.S. Application Data

(63) Continuation of application No. PCT/KR2016/012384, filed on Oct. 31, 2016.

(51) Int. Cl.
*A61N 1/04* (2006.01)
*A61N 1/36* (2006.01)
(Continued)

(52) U.S. Cl.
CPC .......... *A61N 1/36021* (2013.01); *A61B 5/00* (2013.01); *A61B 5/24* (2021.01); *A61N 1/04* (2013.01); *A61N 1/0484* (2013.01); *A61N 1/0492* (2013.01); *A61N 1/08* (2013.01); *A61N 1/36* (2013.01); *A61N 1/36025* (2013.01); *A61N 1/36142* (2013.01); *A61B 5/291* (2021.01); *A61B 5/6803* (2013.01); *A61N 1/0456* (2013.01)

(58) Field of Classification Search
CPC ............ A61N 1/0484; A61N 1/0492; A61N 1/36025; A61N 1/36142; A61N 1/0456
See application file for complete search history.

(56) References Cited

U.S. PATENT DOCUMENTS

| | | | |
|---|---|---|---|
| 2013/0030353 A1* | 1/2013 | Seymour | A61N 5/0622 604/20 |
| 2013/0184779 A1* | 7/2013 | Bikson | A61N 1/36034 607/45 |

(Continued)

FOREIGN PATENT DOCUMENTS

| | | |
|---|---|---|
| KR | 10-2009-0106492 A | 10/2009 |
| KR | 10-2011-0058839 A | 6/2011 |

(Continued)

OTHER PUBLICATIONS

English Translation of KR 101507493 B1 (Year: 2015).*

(Continued)

*Primary Examiner* — Eric D. Bertram
(74) *Attorney, Agent, or Firm* — Studebaker & Brackett PC

(57) ABSTRACT

An electrical stimulation apparatus is provided. The electrical stimulation apparatus includes an electrode module receiving current for applying electrical stimulation to a skin of a user from a current providing part, a plurality of monitoring electrodes positioned spaced apart from each other on the electrode module, the current flows from the electrode module to the plurality of monitoring electrodes, and a current monitoring part monitoring the current flowing to each of the plurality of monitoring electrodes.

13 Claims, 10 Drawing Sheets

(51) Int. Cl.
*A61B 5/00* (2006.01)
*A61N 1/08* (2006.01)
*A61B 5/24* (2021.01)
*A61B 5/291* (2021.01)

(56) References Cited

U.S. PATENT DOCUMENTS

| | | | |
|---|---|---|---|
| 2014/0052199 A1* | 2/2014 | Mohn | A61F 7/02 607/3 |
| 2016/0256105 A1 | 9/2016 | Boyle et al. | |
| 2017/0216593 A1* | 8/2017 | Lee | A61N 1/0492 |

FOREIGN PATENT DOCUMENTS

| | | |
|---|---|---|
| KR | 10-2013-0136487 A | 12/2013 |
| KR | 10-2015-0027810 A | 3/2015 |
| KR | 10-1507493 B1 | 3/2015 |
| KR | 10-1542780 B1 | 8/2015 |
| KR | 10-1566796 B1 | 11/2015 |
| KR | 10-1593067 B1 | 2/2016 |
| KR | 10-1628336 B1 | 6/2016 |
| WO | 2016/064114 A1 | 4/2016 |

OTHER PUBLICATIONS

International Search Report issued in PCT/KR2016/012384; dated Aug. 18, 2017.
The extended European search report issued by the European Patent Office dated Oct. 25, 2019, which corresponds to European Patent Application No. 16919793.6-1124 and is related to U.S. Appl. No. 16/399,003.

* cited by examiner

CURRENT MONITORING APPARATUS AND ELECTRICAL STIMULATION APPARATUS COMPRISING SAME

CROSS-REFERENCE TO RELATED APPLICATIONS

The present application is a continuation of International Patent Application No. PCT/KR2016/012384, filed on Oct. 31, 2016. The disclosure of the above-listed application is hereby incorporated by reference herein in their entirety.

BACKGROUND

Embodiments of the inventive concept described herein relate to a current monitoring apparatus that monitors the amount of current actually flowing to a user's skin for each partitioned area while electrical stimulation is performed, when applying electrical stimulation to a user using an electrical stimulation apparatus, and an electrical stimulation apparatus including the same.

The technology of brain electrical stimulation using transcranial electrical stimulation may be known to be effective in improving cognitive ability and treating mental illnesses such as depression and Attention Deficit Hyperactivity Disorder (ADHD).

When the technology of brain electrical stimulation is available in everyday life, the technology may improve the brain function of a user and may treat continuous mental illness by activating or suppressing the connection between neurons.

SUMMARY

However, according to the conventional electrical stimulation apparatus, the electrical stimulation may be applied to a user based on a preset current value. However, information about how much the current amount is actually transmitted to the user may not be obtained while the electrical stimulation is applied to the user. Accordingly, in the case where the conventional electrical stimulation apparatus is used, even though the large amount of current is instantaneously transmitted to the user due to the unexpected problem of an electrical stimulation apparatus, the user may not recognize and respond to the situation. In some cases, the problem of the safety accident may occur, for example, the case where the user's skin is burnt.

Embodiments of the inventive concept provide a current monitoring apparatus that is capable of preventing the safety accident of a user by monitoring the amount of current actually flowing to the user's skin for each partitioned area to determine whether there is a problem in electrical stimulation when the electrical stimulation is applied to the user by using an electrical stimulation apparatus, and an electrical stimulation apparatus including the same.

Embodiments of the inventive concept provide a current monitoring apparatus that is capable of adjusting the amount of current flowing to the user's skin when the amount of current actually flowing to the user's skin differs from a predetermined reference value, and an electrical stimulation apparatus including the same.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, an electrical stimulation apparatus includes an electrode module receiving current for applying electrical stimulation to a skin of a user from a current providing part, a plurality of monitoring electrodes positioned spaced apart from each other on the electrode module, and a current monitoring part monitoring the current flowing to each of the plurality of monitoring electrodes. The current flows from the electrode module to the plurality of monitoring electrodes.

According to another exemplary embodiment, an electrical stimulation apparatus includes an electrode module receiving current for applying electrical stimulation to a skin of a user from a current providing part, a patch formed on the electrode module, and a current monitoring part monitoring the current transmitted the skin of the user through each area with respect to a plurality of areas on the patch. The patch contacts the skin of the user when the user wears the electrical stimulation apparatus.

According to another exemplary embodiment, a current monitoring apparatus mounted on an electrode module of an electrical stimulation apparatus and monitoring current flowing to a skin of a user by the electrical stimulation apparatus includes a plurality of monitoring electrodes positioned spaced apart from each other on the electrode module and a current monitoring part monitoring the current flowing to each of the plurality of monitoring electrodes. The current is transmitted to the user from the electrode module to the plurality of monitoring electrodes.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
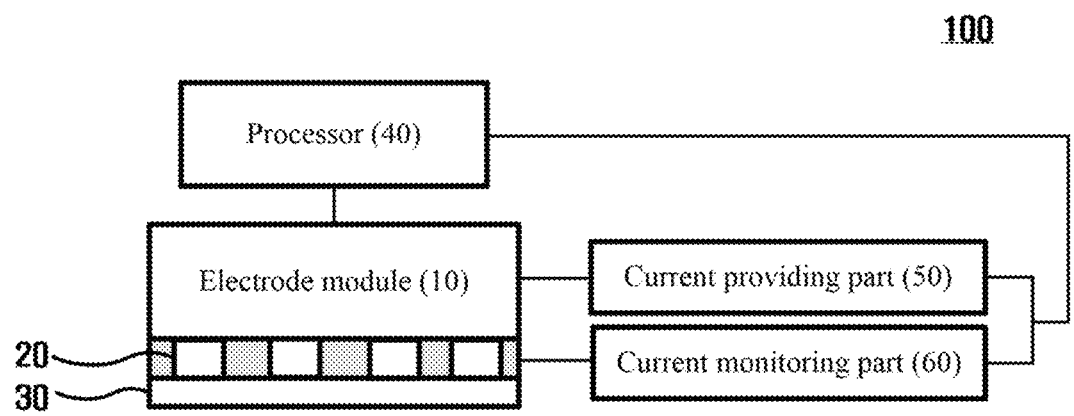
FIG. 1 illustrates an electrical stimulation apparatus, according to the first embodiment of the inventive concept.

Advantage points and features of the inventive concept and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used herein is for the purpose of describing embodiments and is not intended to limit the inventive concept. As used herein, the singular terms are intended to include the plural forms as well, unless the context clearly indicates otherwise. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

As illustrated in the figures, spatially relative terms, such as "below", "beneath", "lower", "above", "upper", and the like, may be used herein for ease of description to describe the relationship between one component and other components. It will be understood that the spatially relative terms are intended to encompass different orientations of the components in use or operation in addition to the orientation depicted in the figures. For example, when inverting a component shown in the figures, a component described as "below" or "beneath" of another component may be placed "above" another element. Thus, the exemplary term "below" may include both downward and upward directions. The components may also be oriented in different directions, and thus the spatially relative terms may be interpreted depending on orientation.

Hereinafter, embodiments of the inventive concept will be described in detail with reference to accompanying drawings.

The electrical stimulation apparatus according to an embodiment of the inventive concept may be a device that applies electrical stimulation to a user's skin (e.g., scalp) to apply transcranial electrical stimulation, and the transcranial electrical stimulation may be transcranial direct current stimulation (tDCS) or transcranial alternating current stimulation (tACS). However, the inventive concept is not limited thereto.

Figure 2:
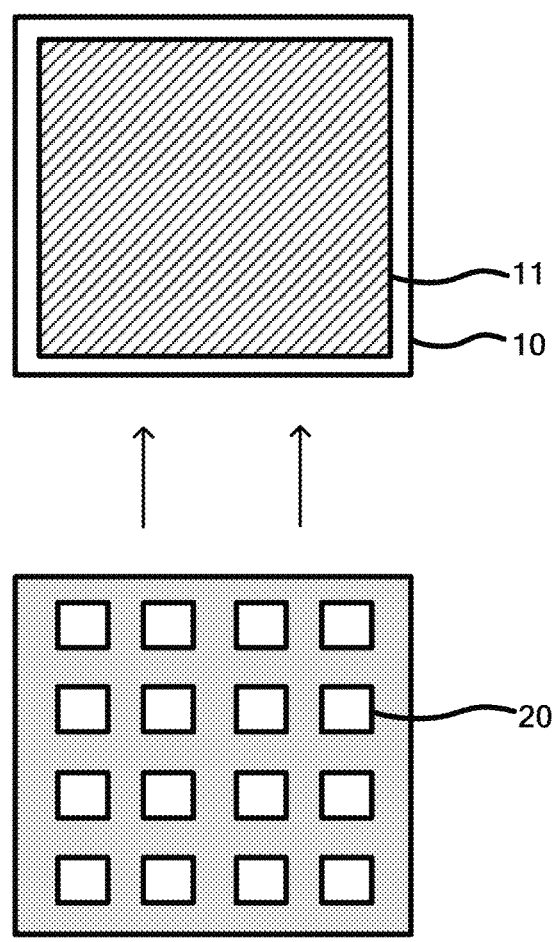
FIG. 2 illustrates a detail diagram of the electrical stimulation apparatus of FIG. 1.
Figure 3:
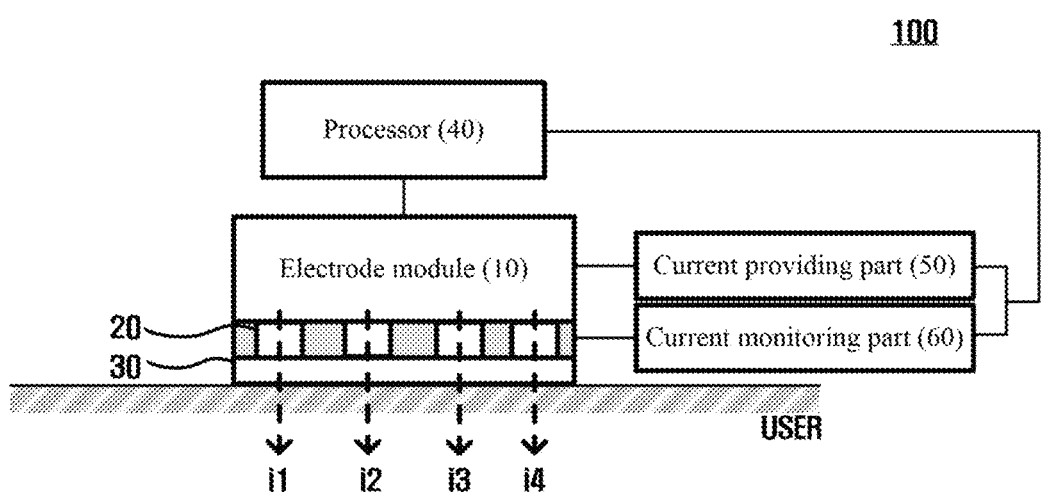
FIG. 3 illustrates a flow of current of an electrical stimulation apparatus of FIG. 1 while electrical stimulation is performed.
Figure 4:
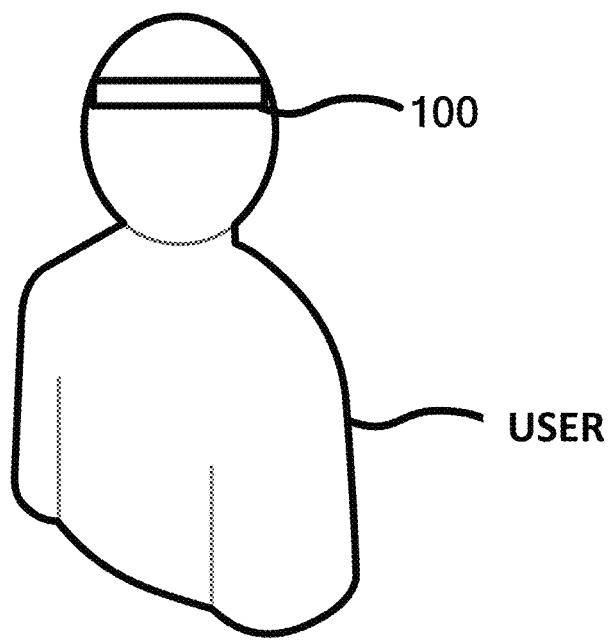
FIG. 4 illustrates a shape in which a user wears the electrical stimulation apparatus of FIG. 1.

The electrical stimulation apparatus according to the first embodiment of the inventive concept will be described with reference to FIGS. 1 to 4. Referring to FIG. 1, the electrical stimulation apparatus according to the first embodiment of the inventive concept is illustrated. Referring to FIG. 2, the detail diagram of the electrical stimulation apparatus of FIG. 1 is disclosed. Referring to FIG. 3, the flow of current of the electrical stimulation apparatus of FIG. 1 is illustrated while the electrical stimulation is performed. Referring to FIG. 4, a shape in which the user wears the electrical stimulation apparatus of FIG. 1 is illustrated.

Referring to FIG. 1, an electrical stimulation apparatus may include an electrode module 10, a plurality of monitoring electrodes 20 and, a patch 30 and may further include a current providing part 50, a current monitoring part 60, and a processor 40 to control an electrical stimulation apparatus. However, the configuration of the electrical stimulation apparatus is not limited thereto. In some embodiments, the electrical stimulation apparatus may include more or fewer components than the components illustrated in FIG. 1.

The electrode module 10 may receive current for applying electrical stimulation the user's skin, from the current providing part 50, and the current of the electrode module 10 may be transmitted to the user through the patch 30. In particular, when the user wears the electrical stimulation apparatus, the patch 30 may contact the user's skin and the electrical stimulation may be applied to the user by using the current of the electrode module 10.

For example, referring to FIG. 2, the electrode module 10 may include an electrode surface 11 that is a conductor, and the current may be transmitted to the patch 30 through the electrode surface 11. Referring to FIG. 3, in a procedure in which the current flows to the patch 30 in the electrode surface 11, the current may be transmitted from the electrode surface 11 to the patch 30 through the monitoring electrodes 20.

The plurality of monitoring electrodes 20 may be arranged spaced apart from each other on the electrode module 10. For example, referring to FIGS. 1 and 2, the plurality of monitoring electrodes 20 may be arranged spaced apart from each other on the electrode surface 11 of the electrode module 10, and the plurality of monitoring electrodes 20 may be distributed uniformly on the electrode module 10. However, the inventive concept is not limited thereto.

Because the current of the electrode module 10 is transmitted to the user's skin through the plurality of monitoring electrodes 20 via the patch 30, when the current flowing to each of the plurality of monitoring electrodes 20 is measured, the amount of current actually transmitted to a user may be measured.

Herein, because the plurality of monitoring electrodes 20 are positioned at different locations on the electrode module 10, when the electrical stimulation apparatus according to an embodiment of the inventive concept is used, the amount of current actually transmitted to the user's skin may be identified through each area with respect to a plurality of areas on the patch 30 contacting the user's skin. As such, in accordance with the electrical stimulation apparatus according to an embodiment of the inventive concept, because it is determined where the problem occurs in locations at which the user's skin is to be stimulated through the electrical stimulation apparatus, the specific and accurate solution to the problem may be derived.

The patch 30 may be removable from the electrode module 20 and may be a replaceable consumable. When the plurality of monitoring electrodes 20 are formed on the electrode module 10, the patch 30 may be removable from the plurality of monitoring electrodes 20. That is, one surface of the patch 30 may contact a user, and the other surface of the patch 30 may cover the plurality of monitoring electrodes 20. Referring to FIGS. 3 and 4, when the patch 30 is attached to the electrode module 10, one surface of the patch 30 may contact the user (e.g., head), and the electrical stimulation may be applied to the user's head by transmitting the current from the plurality of monitoring electrodes 20 to the user through the patch 30.

The patch 30 may include, but is not limited to, a sponge or hydrogel including an electrolyte. Herein, the electrolyte may include chloride ion (Cl−) common to the component of the user's skin. The patch 30 may be formed of a material of impedance higher than the electrode module 10 or the plurality of monitoring electrodes 20.

The single patch 30 may be attached to the single electrode module 10 as the single patch 30. In this case, the plurality of monitoring electrodes 20 may be covered by the patch 30.

The current providing part 50 may be connected to the electrode module 10 to provide the current for electrical stimulation to the electrode module 10. To this end, the current providing part 50 may include a current source/voltage source, a booster circuit, a constant current circuit (e.g., a current regulator diode (CRD), or the like), or the like for providing current for electrical stimulation. However, the inventive concept is not limited thereto.

The current monitoring part 60 may monitor the current flowing to each of the plurality of monitoring electrodes 20 and, for example, may monitor the amount of current flowing to each of the plurality of monitoring electrodes 20. In particular, the current monitoring part 60 may monitor the current transmitted to the user's skin through each of the areas, with respect to a plurality of areas on the patch 30.

To this end, the current monitoring part 60 may include a plurality of Integrated Circuit (IC) chips for measuring the amount of current flowing to each of the monitoring electrodes 20, an analog-to-digital converter (ADC) for converting an analog signal measured by the plurality of IC chips to a digital signal, a micro controller unit (MCU) for processing data and controlling a IC chip. However, the inventive concept is not limited thereto.

The processor 40 may control the operation of the electrical stimulation apparatus as a whole. For example, firmware for performing a control operation may be provided in the processor 40. The processor 40 may receive the result of monitoring the current from the current monitoring part 60 and may generate an alarm signal to interrupt the operation of an electrical stimulation apparatus or to warn the user depending on the result of monitoring the current. However, the operation of the processor 40 is not limited thereto.

Hereinafter, the operation of an electrical stimulation apparatus according to the first embodiment of the inventive concept will be described.

When the user wears the electrical stimulation apparatus and then the electrical stimulation is applied to the user through the electrical stimulation apparatus, the current monitoring part 60 may measure the amount of current flowing to each of the plurality of monitoring electrodes 20. That is, when the electrical stimulation apparatus according to an embodiment of the inventive concept is used, it may be determined how much the current flows to the user's skin corresponding to the area in which the plurality of monitoring electrodes 20 are positioned.

For example, when there is acne or a scar on the user's skin contacting the patch 30, the corresponding region may have lower resistance than other region due to the impairment of dead skin cells. As such, the large amount of current may flow to the corresponding region. Furthermore, when the deterioration of the patch 30 lowers the resistance of the partial area of the patch 30 or when the partial area of the patch 30 does not stick to the user's skin, the resistance of the corresponding area may be lower than that of another area. Accordingly, the large amount of current may flow to the corresponding area.

For various reasons, when the part of the current amount measured from the plurality of monitoring electrodes 20 differs from the other part of the current amount, the electrical stimulation apparatus may recognize that the corresponding case is problematic. Accordingly, the electrical stimulation apparatus may take action to resolve the problem.

Most of all, the processor 40 may recognize the case where the monitoring result of the current monitoring part 60 indicates that the amount of current flowing to the at least one monitoring electrode 20 is less or greater than a predetermined reference current amount, as the problematic situation in the electrical stimulation apparatus.

That is, when the amount of current flowing to the at least one monitoring electrode 20 is less than the predetermined reference current amount, this may be recognized as a problem that a user may be burned because too much current amount may flow to a specific area. Moreover, when the amount of current flowing to the at least one monitoring electrode 20 is greater than the predetermined reference current amount, because the excessive amount of current may flow to the other monitoring electrode 20 due to the current, the amount of which is less than the reference current amount, flowing to the monitoring electrode 20, this may be recognized as a situation in which the user may be burned.

Furthermore, for that reasons the same as details described above, the processor 40 may recognize the case where the monitoring result of the current monitoring part 60 indicates that the amount of current flowing to the one monitoring electrode 20 is less or greater than a specific ratio, as the problematic situation in the electrical stimulation apparatus.

As such, when the processor 40 recognizes that there is a problem with the electrical stimulation apparatus, by analyzing the monitoring result of the current monitoring part 60, the processor 40 may interrupt the electrical stimulation by the electrical stimulation apparatus, by interrupting the providing the current from the electrode providing part.

Accordingly, when the electrical stimulation apparatus according to an embodiment of the inventive concept is used, in the case where the electrical stimulation is applied to the user by using the electrical stimulation apparatus, the amount of current actually flowing to the user's skin may be monitored for each partitioned area. As such, the electrical stimulation may be interrupted, if necessary, to prevent the safety accident of the user, by determining whether there is a problematic area in electrical stimulation.

Figure 5:
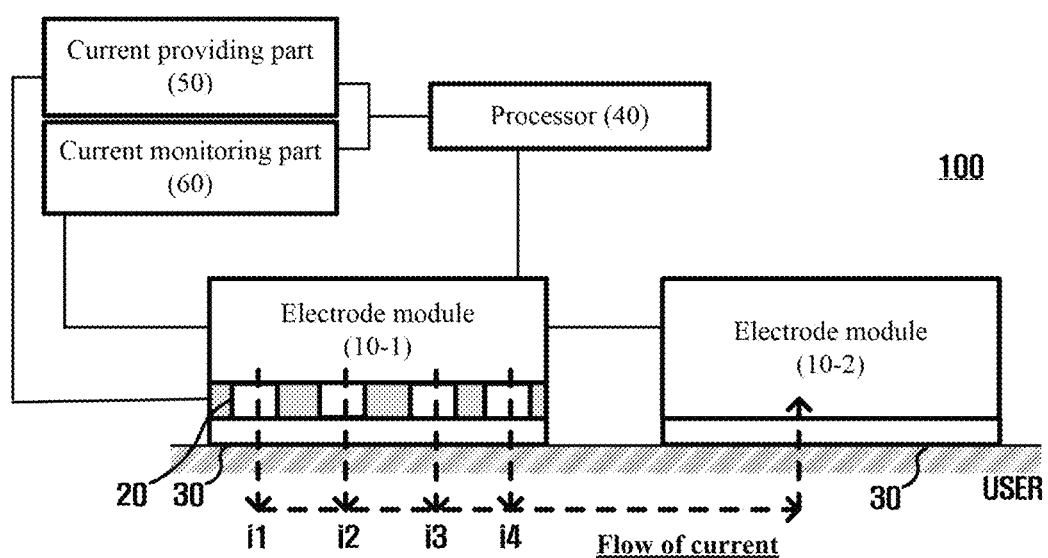
FIG. 5 illustrates an electrical stimulation apparatus, according to the second embodiment of the inventive concept.
Figure 6:
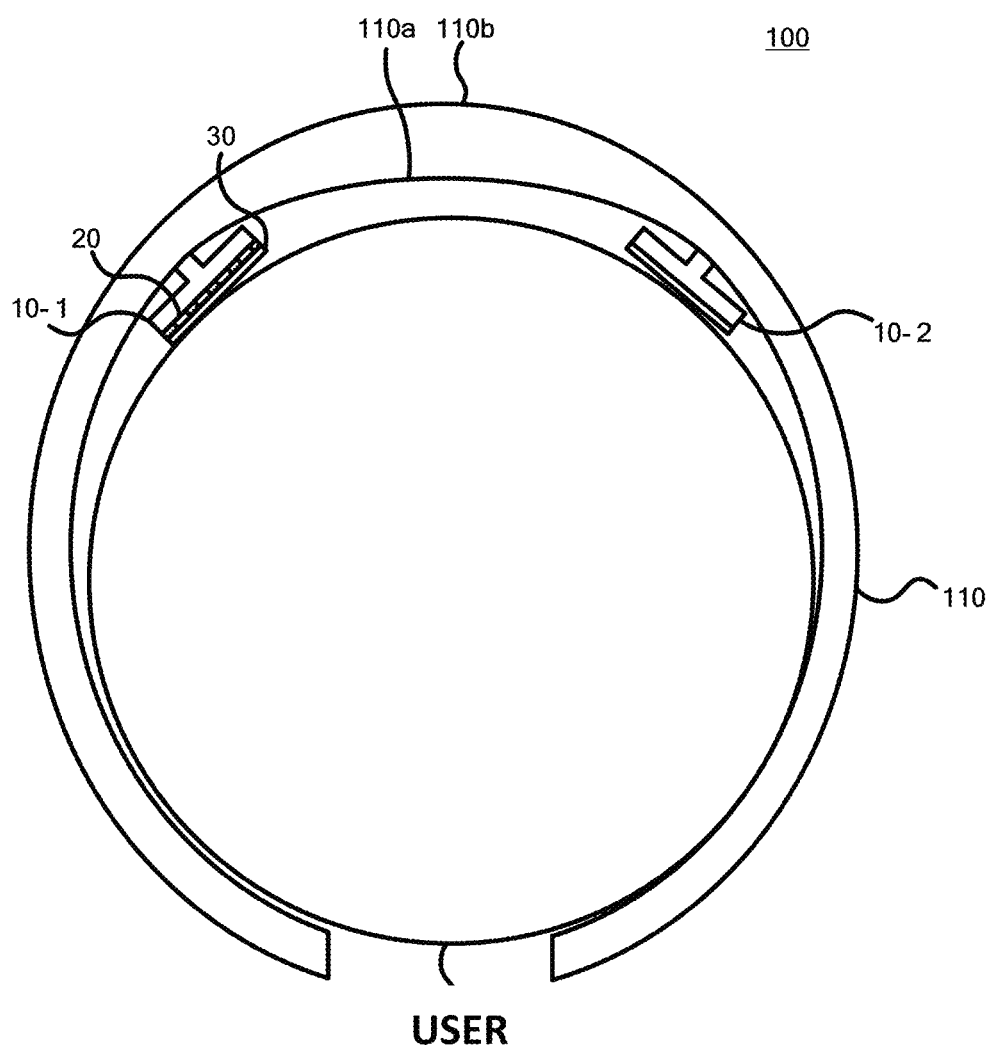
FIG. 6 illustrates an exemplary view of an electrical stimulation apparatus, according to the second embodiment of the inventive concept.

The electrical stimulation apparatus according to the second embodiment of the inventive concept will be described with reference to FIGS. 5 and 6. However, the difference from the electrical stimulation apparatus according to the first embodiment of the inventive concept will be described mainly. Referring to FIG. 5, the electrical stimulation apparatus according to the second embodiment of the inventive concept is illustrated. Referring to FIG. 6 an exemplary view of an electrical stimulation apparatus, according to the second embodiment of the inventive concept is illustrated.

Referring to FIG. 5, an electrode stimulation apparatus in the electrical stimulation apparatus according to an embodiment of the inventive concept may include a plurality of electrode modules 10-1 and 10-2. Herein, a part of the electrode module 10-1 is an anode, and a part of the electrode module 10-2 is a cathode.

The plurality of monitoring electrodes 20 may be positioned on only the electrode module 10-1 among the plurality of electrode modules 10-1 and 10-2. In particular, the plurality of monitoring electrodes 20 may be positioned on only the electrode module 10-1, which is an anode, from among the plurality of electrode modules 10-1 and 10-2 and may not be positioned on the electrode module 10-2, which is a cathode.

In the electrical stimulation apparatus according to an embodiment of the inventive concept, because the plurality of monitoring electrodes 20 are positioned on the electrode module 10-1 that is an anode, the amount of current provided to the user's skin may be monitored for each partitioned area In the meantime, referring to FIG. 6 an exemplary view of an electrical stimulation apparatus according to an embodiment of the inventive concept is illustrated.

The frame 110 may be the frame of the electrical stimulation apparatus. For example, various components such as the electrode module 10, the processor 40, and the like may be connected to the frame 110 or may be embedded in the frame 110. However, the inventive concept is not limited thereto.

The frame 110 may include a first surface 110a facing the user's head and a second surface 110b positioned opposite to the first surface 110a. Moreover, the frame 110 may have a shape capable of being worn on the user's head and may be worn and fixed to the user, due to the structural features of the frame 110. For example, the frame 110 may have a ring structure, one side of which is opened. However, the inventive concept is not limited thereto.

Because the frame 110 compresses the head due to the structural features of the frame 110 when the frame 110 is worn on the user's head, the frame 110 may be stably fixed to the user's head without falling downward by gravity. In some embodiments, the partial area of the frame 110 may be supported on the user's auricle such that the frame 110 may be stably worn on the user's head. However, in the case of the frame 110 of the shape capable of being worn on the head due to the structural feature, the shape of the frame 110 is not limited thereto.

Figure 7A:
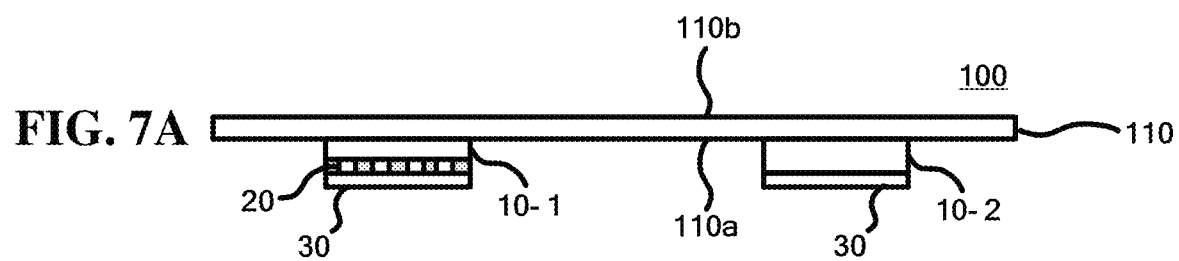
FIGS. 7A and 7B illustrate exemplary views of an electrical stimulation apparatus, according to the third embodiment of the inventive concept.
Figure 7B:
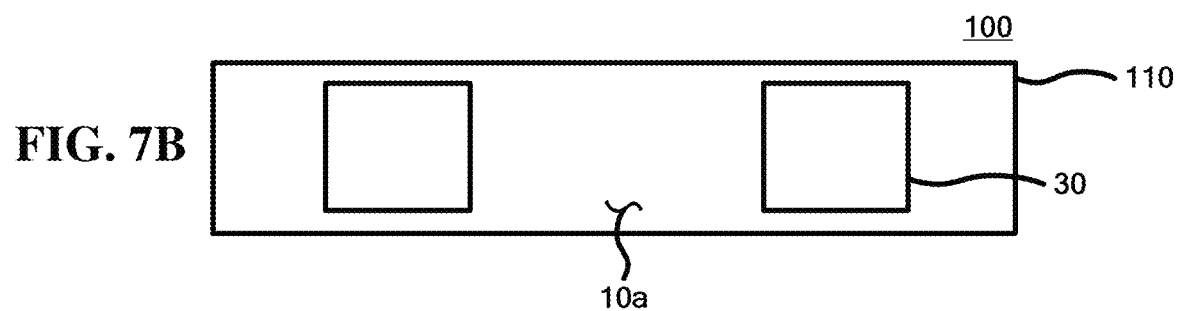

The electrical stimulation apparatus according to the third embodiment of the inventive concept will be described with reference to FIGS. 7A and 7B. However, the difference from the electrical stimulation apparatus according to the second embodiment of the inventive concept will be described mainly. Referring to FIGS. 7A and 7B exemplary views of an electrical stimulation apparatus, according to the third embodiment of the inventive concept is illustrated.

Referring to FIGS. 7A and 7B, the frame 110 may be worn by a user in an adhesive manner. To this end, for example, the first surface 110a of the frame 110 may include, but is not limited to, an adhesive. Moreover, the electrical stimulation apparatus according to an embodiment of the inventive concept may have a difference in the wearing method from the electrical stimulation apparatus according to the second embodiment of the inventive concept, and thus the electrical stimulation apparatus according to the second embodiment of the inventive concept may be applied as it is.

Figure 8:
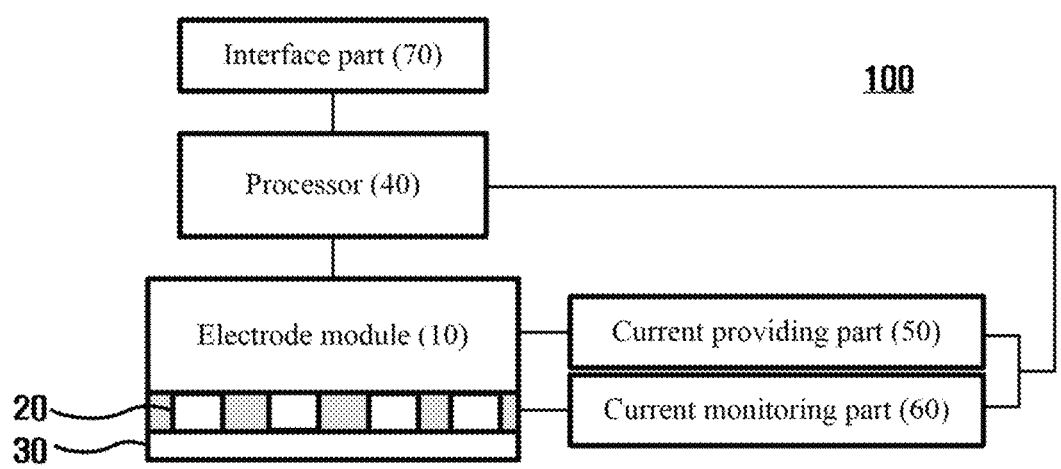
FIG. 8 illustrates an electrical stimulation apparatus, according to the fourth embodiment of the inventive concept.

The electrical stimulation apparatus according to the fourth embodiment of the inventive concept will be described with reference to FIG. 8. However, the difference from the electrical stimulation apparatus according to the first embodiment of the inventive concept will be described mainly. Referring to FIG. 8, the electrical stimulation apparatus according to the fourth embodiment of the inventive concept is illustrated.

Referring to FIG. 8, the electrical stimulation apparatus according to an embodiment of the inventive concept may include an interface part 70. The interface part 70 may interface with the user. In particular, the interface part 70 may receive various types of information from the user and may output the various types of information to the user. To the end, the interface part 70 may include an input means such as a keypad, a button, a switch, a touch pad, a jog wheel, or the like, and the interface part 70 may include an output means such as a display module, a speaker module, an optical module, a vibration module, a haptic module, or the like.

Herein, the display module may be provided in the form of any type such as a plasma display panel (PDP), an liquid crystal display (LCD), a thin film transistor (TFT) LCD, an organic light emitting diode (OLED) display, a flexible display, a three-dimensional (3D) display, or the like.

Hereinafter, the operation of an electrical stimulation apparatus according to the fourth embodiment of the inventive concept will be described.

As described above, the processor 40 may recognize the case where the monitoring result of the current monitoring part 60 indicates that the amount of current flowing to the at least one monitoring electrode 20 is less or greater than a predetermined reference current amount, as the problematic situation in the electrical stimulation apparatus. The processor 40 may recognize the case where the monitoring result of the current monitoring part 60 indicates that the amount of current flowing to the one monitoring electrode 20 is less or greater than a specific ratio, as the problematic situation in the electrical stimulation apparatus.

As such, when the processor 40 recognizes that there is a problem with the electrical stimulation apparatus, by analyzing the monitoring result of the current monitoring part 60, the processor 40 may generate an alarm signal for an operational error of the electrical stimulation apparatus. The alarm signal generated by the processor 40 may be transmitted to the interface part 70 and may be output as sound, light, vibration, or the like through a speaker module, an optical module, a vibration module, or the like. As such, the user may recognize that there is a problem with the electrical stimulation apparatus and then may remove the electrical stimulation apparatus or interrupt the electrical stimulation apparatus.

Figure 9:
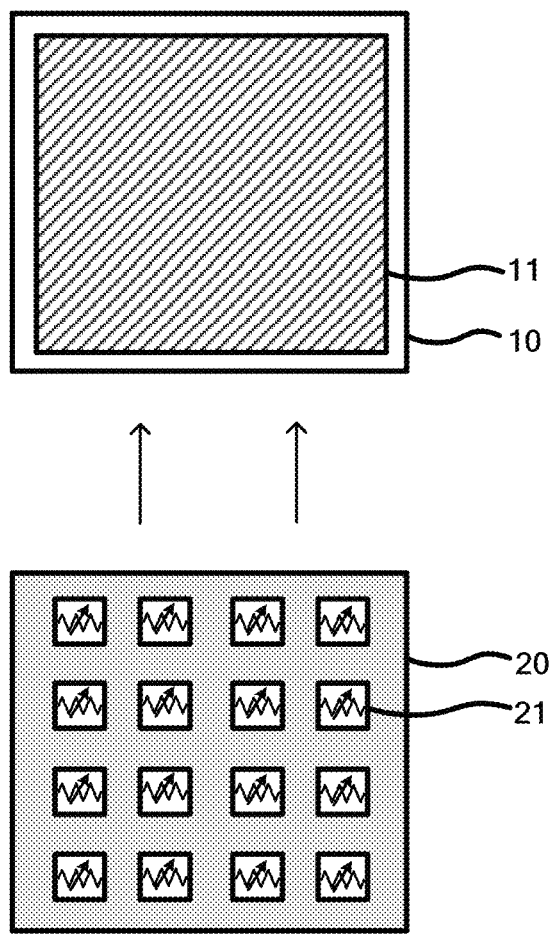
FIG. 9 illustrates an electrical stimulation apparatus, according to the fifth embodiment of the inventive concept.

The electrical stimulation apparatus according to the fifth embodiment of the inventive concept will be described with reference to FIG. 9. However, the difference from the electrical stimulation apparatus according to the first embodiment of the inventive concept will be described mainly. Referring to FIG. 9, the electrical stimulation apparatus according to the fifth embodiment of the inventive concept is illustrated.

Referring to FIG. 9, each of the plurality of monitoring electrodes 20 may include a variable resistor 21. Accordingly, when the electrical stimulation apparatus according to an embodiment of the inventive concept requires the variable resistor, the magnitude of current transmitted to the user's skin from the electrode module 10 may be adjusted for each partitioned area, by controlling the variable resistor 21 included in each of the plurality of monitoring electrodes 20.

Hereinafter, the operation of an electrical stimulation apparatus according to the fifth embodiment of the inventive concept will be described.

As described above, the processor 40 may recognize the case where the monitoring result of the current monitoring part 60 indicates that the amount of current flowing to the at least one monitoring electrode 20 is less or greater than a predetermined reference current amount, as the problematic situation in the electrical stimulation apparatus. The processor 40 may recognize the case where the monitoring result of the current monitoring part 60 indicates that the amount of current flowing to the one monitoring electrode 20 is less or greater than a specific ratio, as the problematic situation in the electrical stimulation apparatus.

As such, when the processor 40 recognizes that there is a problem with the electrical stimulation apparatus, by analyzing the monitoring result of the current monitoring part 60, the processor 40 may adjust the amount of current flowing to at least one monitoring electrode 20. In particular, the processor 40 may adjust the size of the variable resistor 21 included in the at least one monitoring electrode 20, to adjust the amount of current flowing to at least one monitoring electrode 20.

For example, when the processor 40 determines that the amount of current flowing to any monitoring electrode 20 is less than a predetermined reference current amount, the processor 40 may increase the size of the variable resistor 21 of the corresponding monitoring electrode 20. As such, as the size of the variable resistor 21 increases, the amount of current flowing to the corresponding monitoring electrode 20 may be reduced, thereby preventing safety accidents that may occur to the user due to excessive current.

Figure 10:
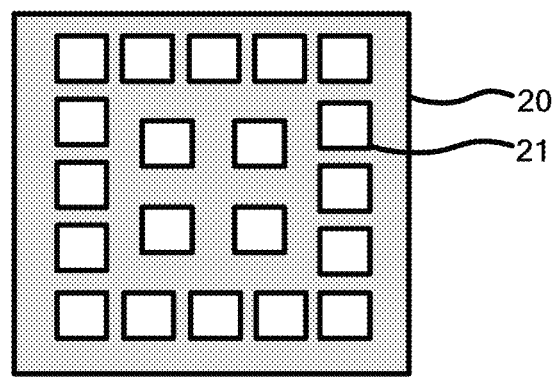
FIG. 10 illustrates an electrical stimulation apparatus, according to the sixth embodiment of the inventive concept.

The electrical stimulation apparatus according to the sixth embodiment of the inventive concept will be described with reference to FIG. 10. However, the difference from the electrical stimulation apparatus according to the first embodiment of the inventive concept will be described mainly. Referring to FIG. 10, the electrical stimulation apparatus according to the sixth embodiment of the inventive concept is illustrated.

Referring to FIG. 2, it is disclosed that the plurality of monitoring electrodes 20 are uniformly distributed on the electrode module 10. Meanwhile, referring to FIG. 10, the plurality of monitoring electrodes 20 may be nonuniformly distributed on the electrode module 10. For example, the patch 30 may fail to stick to the user due to deterioration of the patch 30. In particular, the patch 30 may have poor adhesion at the edge of the patch 30 rather than the center of the patch 30.

In this case, it is possible to precisely monitor the adhesion failure of the patch 30 by making the density of the monitoring electrode 20, which is positioned at the center of the electrode module 10, smaller than the density of the monitoring electrode 20 positioned at the periphery of the electrode module 10. However, the plurality of nonuniformly distributed electrodes 20 on the electrode module 10 are not limited as having this arrangement.

Figure 11:
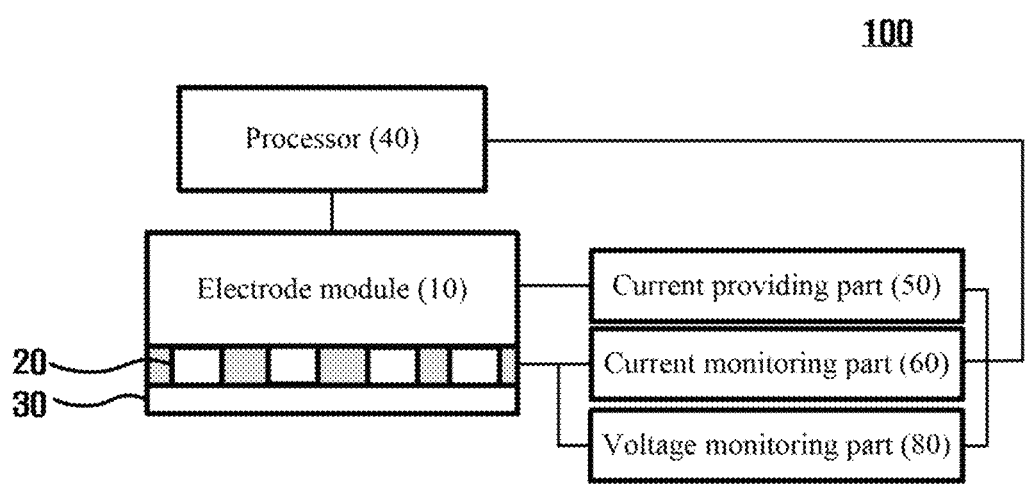
FIG. 11 illustrates an electrical stimulation apparatus, according to the seventh embodiment of the inventive concept.

The electrical stimulation apparatus according to the seventh embodiment of the inventive concept will be described with reference to FIG. 11. However, the difference from the electrical stimulation apparatus according to the first embodiment of the inventive concept will be described mainly. Referring to FIG. 11, the electrical stimulation apparatus according to the seventh embodiment of the inventive concept is illustrated.

Referring to FIG. 11, an electrical stimulation apparatus according to an embodiment of the inventive concept may further include a voltage monitoring part 80 that monitors the voltage applied to the plurality of monitoring electrodes 20. Herein, because the plurality of monitoring electrodes 20 are connected, for example, in parallel, the current flowing to each of the plurality of monitoring electrodes 20 may be different, but the voltage applied to each of the plurality of monitoring electrodes 20 may be the same.

The processor 40 may receive information about the voltage applied to the plurality of monitoring electrodes 20, from the voltage monitoring part 80; when the monitoring result of the voltage monitoring part 80 indicates that the voltage applied to the plurality of monitoring electrodes 20 is less or greater than a predetermined reference voltage, the processor 40 may interrupt the providing of the current from the current providing part, thereby preventing safety accidents that may occur to the user.

Figure 12:
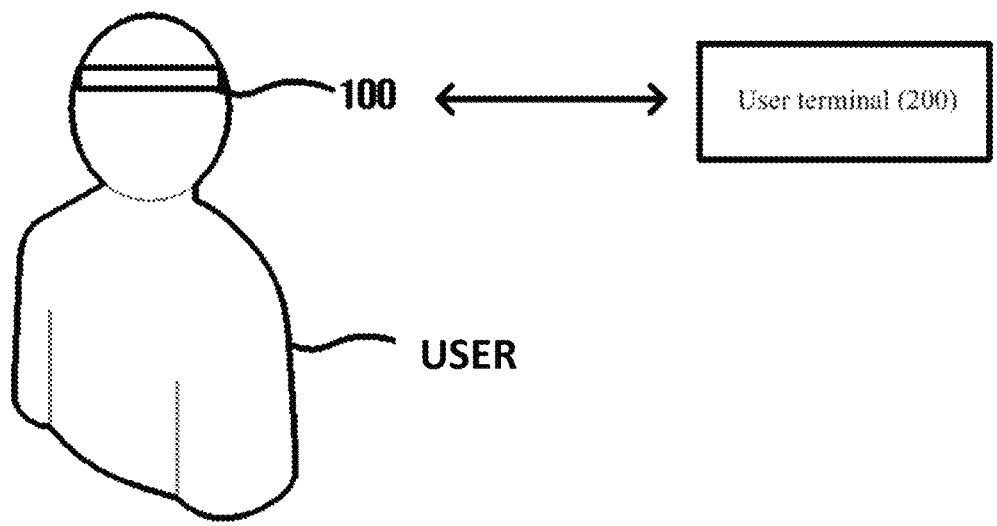
FIG. 12 illustrates an electrical stimulation system, according to an embodiment of the inventive concept.

An electrical stimulation system according to an embodiment of the inventive concept will be described with reference to FIG. 12. However, the electrical stimulation apparatus included in the electrical stimulation system according to an embodiment of the inventive concept may be one of the above-described electrical stimulation apparatuses. Referring to FIG. 12, the electrical stimulation system according to an embodiment of the inventive concept will be described.

Referring to FIG. 12, the electrical stimulation system may include an electrical stimulation apparatus and a user terminal 200, and the electrical stimulation apparatus and the user terminal 200 may communicate with each other. For example, the alarm signal generated from the processor 40 of the electrical stimulation apparatus may be transmitted to the outside user terminal 200 through a communication device (not illustrated) of the electrical stimulation apparatus, and then the alarm signal may be output through the user terminal 200.

Furthermore, the current monitoring result or the voltage monitoring result generated from the current monitoring part 60 or the voltage monitoring part 80 of the electrical stimulation apparatus may be transmitted to the outside user terminal 200 through the communication device (not illustrated) of the electrical stimulation apparatus, and then the monitoring result may be output through the user terminal 200. For example, the monitoring result may be output as a specific number. However, the inventive concept is not limited thereto. The monitoring result may also be imaged and output via a graph or color schemes.

In the meantime, in some embodiments, the communication device (not illustrated) of the electrical stimulation apparatus may not directly communicate with the outside user terminal 200, and may communicate with the outside user terminal 200 via a server (not illustrated).

Figure 13:
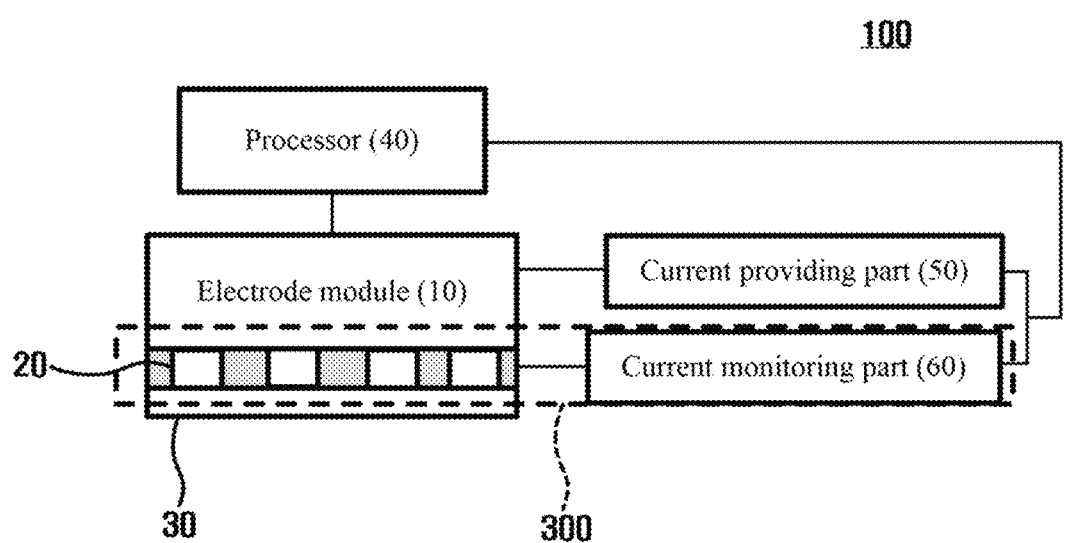
FIG. 13 illustrates a current monitoring apparatus, according to the first embodiment of the inventive concept.

Hereinafter, a current monitoring apparatus 300 according to the first embodiment of the inventive concept will be described with reference to FIG. 13. However, the same configuration as that described in the electrical stimulation apparatus according to embodiments of the inventive concept will be described briefly, and a portion where the description is omitted may also be applied to the current monitoring apparatus 300 according to an embodiment of the inventive concept. Referring to FIG. 13, the current monitoring apparatus 300 according to the first embodiment of the inventive concept is illustrated.

Referring to FIG. 13, the configuration necessary for current monitoring in the electrical stimulation apparatus according to embodiments of the inventive concept may be configured as a separate current monitoring apparatus 300. The current monitoring apparatus 300 may be removed from the electrical stimulation apparatus. As such, if necessary, the current monitoring apparatus 300 may be mounted on the electrical stimulation apparatus to monitor the current.

For example, the current monitoring apparatus 300 may be mounted on the electrode module 10 of the electrical stimulation apparatus to monitor the current flowing to the user's skin by the electrical stimulation apparatus, and the current monitoring apparatus 300 may include the plurality of monitoring electrodes 20 and the current monitoring part 60.

The plurality of monitoring electrodes 20 may be positioned spaced apart from each other on the electrode module 10 and the current may be transmitted from the electrode module 10 to the user through the plurality of monitoring electrodes 20. Moreover, the current monitoring part 60 may monitor the current flowing to each of the plurality of monitoring electrodes 20 and, in particular, may monitor the amount of current flowing to each of the plurality of monitoring electrodes 20.

In some embodiments, each of the plurality of monitoring electrodes 20 may include a variable resistor 21.

Figure 14:
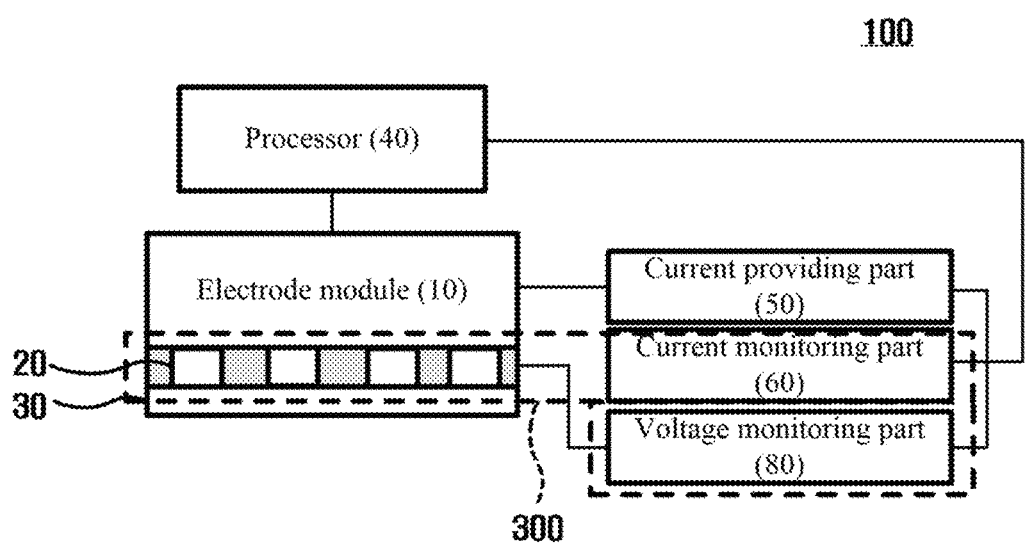
FIG. 14 illustrates a current monitoring apparatus, according to the second embodiment of the inventive concept.

The current monitoring apparatus 300 according to the second embodiment of the inventive concept will be described with reference to FIG. 14. However, the difference from the current monitoring apparatus 300 according to the first embodiment of the inventive concept will be described mainly. Referring to FIG. 14, the current monitoring apparatus 300 according to the second embodiment of the inventive concept is illustrated.

Referring to FIG. 14, the current monitoring apparatus 300 according to an embodiment of the inventive concept may further include a voltage monitoring part 80 that monitors the voltage applied to the plurality of monitoring electrodes 20.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, it should be understood that the above embodiments are not limiting, but illustrative.

First, according to an embodiment of the inventive concept, the amount of current actually flowing to a user's skin may be monitored for each partitioned area when electrical stimulation is applied to the user by using an electrical stimulation apparatus.

Second, the safety accident of the user may be prevented by monitoring the amount of current actually flowing to the user's skin for each partitioned area to determine whether there is a problem in electrical stimulation.

Third, when there is a problem that the amount of current actually flowing to the user's skin differs from the predetermined reference value, the amount of current flowing to the user's skin may be adjusted.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An electrical stimulation apparatus comprising:
   an anode electrode module having a T-shape, and configured to receive current for applying electrical stimulation to a skin of a user from a current providing part;
   a cathode electrode module having a T-shape, and spaced apart from the anode electrode;
   a plurality of monitoring electrodes, positioned only on the anode electrode module and positioned spaced apart from each other, wherein the current flows from the anode electrode module to the plurality of monitoring electrodes, and wherein the cathode electrode module does not have any monitoring electrode;
   a current monitoring part configured to monitor the current flowing to each of the plurality of monitoring electrodes;
   a processor configured to receive monitoring results from the current monitoring part; and
   an interface part configured to
      receive information from the user and the processor, and
      output information via at least one of a display module, a speaker module, an optical module, a vibration module and a haptic module,
   wherein the processor is further configured to generate, in response to a detection that the monitoring results received by the processor indicate that an amount of current flowing to at least one monitoring electrode of the plurality of monitoring electrodes is less or greater than a predetermined current amount, an alarm signal indicating an operational error of the electrical stimulation apparatus, and transmits the generated alarm signal to the interface part, and
   wherein the plurality of monitoring electrodes are non-uniformly distributed on the anode electrode module such that a first density of first monitoring electrodes, which are positioned at a center portion of the anode electrode module, is smaller than a second density of second monitoring electrodes, which are positioned at a periphery portion of the anode electrode module.

2. The electrical stimulation apparatus of claim 1, wherein the plurality of monitoring electrodes are positioned spaced apart from each other on an electrode surface of the anode electrode module.

3. The electrical stimulation apparatus of claim 1, further comprising:

a patch, one surface of which contacts the user and the other surface of which covers the plurality of monitoring electrodes, wherein the current is transmitted from the plurality of monitoring electrodes to the user through the patch.

4. The electrical stimulation apparatus of claim 3, wherein the patch includes a sponge or hydrogel.

5. The electrical stimulation apparatus of claim 1, wherein, when the monitoring result of the current monitoring part indicates that an amount of current flowing to at least one monitoring electrode is less or greater than the predetermined current amount, provision of the current from the current providing part is interrupted.

6. The electrical stimulation apparatus of claim 1, wherein, when the monitoring result of the current monitoring part indicates that an amount of current flowing to at least one monitoring electrode is less or greater than the predetermined current amount, an amount of current flowing the at least one monitoring electrode is adjusted.

7. The electrical stimulation apparatus of claim 6, wherein each of the plurality of monitoring electrodes includes a variable resistor, and wherein the adjusting of the amount of current flowing the at least one monitoring electrode includes adjusting a size of the variable resistor included in the at least one monitoring electrode.

8. The electrical stimulation apparatus of claim 1, wherein, when the monitoring result of the current monitoring part indicates that a result of comparing an amount of current flowing to one monitoring electrode with an amount of current flowing to another monitoring electrode is less or greater than a specific ratio, provision of the current from the current providing part is interrupted.

9. The electrical stimulation apparatus of claim 1, wherein, when the monitoring result of the current monitoring part indicates that a result of comparing an amount of current flowing to one monitoring electrode with an amount of current flowing to another monitoring electrode is less or greater than a specific ratio, the alarm signal is generated.

10. The electrical stimulation apparatus of claim 1, wherein, when the monitoring result of the current monitoring part indicates that a result of comparing an amount of current flowing to one monitoring electrode with an amount of current flowing to another monitoring electrode is less or greater than a specific ratio, an amount of current flowing the one monitoring electrode is adjusted.

11. The electrical stimulation apparatus of claim 10, wherein each of the plurality of monitoring electrodes includes a variable resistor, and wherein the adjusting of the amount of current flowing the at least one monitoring electrode includes adjusting a size of the variable resistor included in the at least one monitoring electrode.

12. The electrical stimulation apparatus of claim 1, further comprising:

a voltage monitoring part configured to monitor voltage applied to the plurality of monitoring electrodes.

13. The electrical stimulation apparatus of claim 12, wherein, when the monitoring result of the voltage monitoring part indicates that the voltage applied to the plurality of monitoring electrodes is less or greater than a predetermined reference voltage, provision of current from the current providing part is interrupted.

* * * * *